United States Patent [19]
Kolber et al.

[11] Patent Number: 5,171,214
[45] Date of Patent: Dec. 15, 1992

[54] DRUG STORAGE AND DELIVERY SYSTEM

[75] Inventors: Chris M. Kolber, Nashua, N.H.; Peter L. Bryant, Lake Forest; Mark E. Larkin, Lindenhurst; Peter J. Karas, Libertyville; John S. Ziegler, Arlington Heights, all of Ill.

[73] Assignee: Abbott Laboratories, Abbott Park, Ill.

[21] Appl. No.: 634,275

[22] Filed: Dec. 26, 1990

[51] Int. Cl.$^5$ .............................................. A61M 37/00
[52] U.S. Cl. ........................................ 604/82; 604/88; 604/411; 604/905; 222/82; 215/355; 215/247; 206/222
[58] Field of Search ...................... 604/82, 86, 87, 88, 604/92, 411, 412, 416, 415, 905, 200–203; 141/27; 222/82, 83, 83.5, 135, 136, 129; 206/222; 215/DIG. 8, 355, 247

[56] References Cited

U.S. PATENT DOCUMENTS

| | | | |
|---|---|---|---|
| 3,397,694 | 8/1968 | Ogle | 604/88 |
| 3,542,023 | 11/1970 | Ogle | 604/88 |
| 3,547,122 | 12/1970 | Rinser et al. | 604/88 |
| 3,563,373 | 2/1971 | Paulson | 604/88 X |
| 3,570,486 | 3/1971 | Engelsher | 604/88 |
| 3,659,602 | 5/1972 | Cloyd | 604/88 |
| 3,730,392 | 5/1973 | Marand | 222/82 |
| 3,977,555 | 8/1976 | Larson | 604/411 X |
| 3,995,630 | 12/1976 | vande Veerdonk | 604/92 X |
| 4,146,153 | 3/1979 | Bailen | 222/83 |
| 4,346,820 | 8/1982 | Cavazza | 222/83 |
| 4,505,709 | 3/1985 | Froning et al. | 604/411 |
| 4,516,967 | 5/1985 | Kopfer | 604/87 |
| 4,568,346 | 2/1986 | van Dijk | 604/414 |
| 4,576,211 | 3/1986 | Valentini et al. | 141/329 |
| 4,607,671 | 8/1986 | Aalto et al. | 141/329 |
| 4,619,651 | 10/1986 | Kopfer et al. | 604/415 |
| 4,648,532 | 3/1987 | Green | 222/82 |
| 4,759,756 | 7/1988 | Forman et al. | 604/413 |
| 4,768,568 | 9/1888 | Fournier et al. | 141/286 |
| 4,773,529 | 9/1988 | Finke et al. | 206/222 |
| 4,785,858 | 11/1988 | Valentini et al. | 141/27 |
| 4,787,429 | 11/1988 | Valentini et al. | 141/383 |
| 4,801,009 | 1/1989 | Amus | 206/222 |
| 4,861,335 | 8/1989 | Reynolds | 604/88 |
| 4,886,495 | 12/1989 | Reynolds | 604/88 |
| 4,898,293 | 2/1990 | Morel | 215/250 |
| 4,994,029 | 2/1991 | Rohrbough | 604/88 |
| 5,019,052 | 5/1991 | Rohrbough | 604/203 |
| 5,020,220 | 6/1991 | Miyake et al. | 30/2 |
| 5,037,390 | 8/1991 | Raines | 604/88 |
| 5,045,081 | 9/1991 | Dyserz | 604/411 |
| 5,088,996 | 2/1992 | Kopfer et al. | 604/415 |

FOREIGN PATENT DOCUMENTS

0327519 8/1989 European Pat. Off. ............ 604/411

Primary Examiner—C. Fred Rosenbaum
Assistant Examiner—Mark O. Polutta
Attorney, Agent, or Firm—A. Nicholas Trausch

[57] ABSTRACT

A drug storage and delivery system that includes a drug containing vial assembly, a syringe assembly, and an adapter assembly for attaching the vial assembly to the adapter assembly. The vial assembly includes a vial that is provided with a pierceable stopper and a skirt member that circumscribes the outside of the vial. The syringe assembly includes a cannula extending longitudinally therethrough. The adapter assembly attaches the vial assembly to the syringe assembly in a manner that permits communication between the interior of the vial and the cannula extending through the syringe. The system also permits attachment of the syringe assembly to a container filled with a diluent and means for delivering the diluent into the vial assembly and subsequently directing the mixed solution back into the container.

23 Claims, 5 Drawing Sheets

DRUG STORAGE AND DELIVERY SYSTEM

BACKGROUND OF THE INVENTION

1. Field Of The Invention

This invention relates to a drug storage and delivery system that affords sterile access and delivery of the contents of a drug-containing vial assembly. More particularly, the invention relates to a drug storage and delivery system that includes a unique adapter assembly to connect a drug-containing vial assembly to a syringe assembly used to transfer a diluent into the vial assembly and/or to transfer the contents from the vial assembly.

2. Description Of The Prior Art

Medicaments or drugs normally administered in a health care environment, being flowable substances, are typically packaged in vials whose interior is maintained in a sterile condition. The vials themselves are sealed by a sterile stopper that is eventually pierced by a cannula when it is desired to remove the medicament or drug. Several procedures are required in order to remove the drug from the vial and administer it to a patient. Each procedure is time consuming for health care personnel and more importantly each procedure presents a risk of jeopardizing the sterility of the vial, the stopper or the medicament.

If the drug in a particular vial is a powder, the procedures that may jeopardize sterility include adding diluent to the vial to dissolve the powder, withdrawing the reconstituted drug from the vial, and then subsequently further diluting the concentrated drug solution to the desired strength. When the medicament or drug can be administered directly to a patient, a cannula and syringe assembly may be used to make an injection through the skin of the patient or into a Y-site in an I.V. administration set. If the medicament or drug is of such a strength or potency that it must be administered over a prolonged period of time then the medicament or drug is mixed with a large quantity of diluent and placed into a container which becomes a secondary fluid source in a piggyback I.V. administration system. Alternatively, the reconstituted drug may be administered from a syringe using an electromechanical pump. If there is no primary fluid source in an I.V. administration system the drug and diluent solution may itself be administered intravenously to a patient.

The problem, therefore, experienced by health care and pharmacy personnel with prior art drug delivery systems is three-fold. First, multiple time consuming procedures are required in order to take the drug from its storage condition in a pharmacy to a condition in which it can be properly and safely administered to a patient. Second, each procedure between storage and administration presents a new opportunity for jeopardizing drug, stopper or vial sterility. Third, the time between mixing and use is limited to typically one day, due to loss of potency for the mixed drug.

A system is disclosed for storage and delivery of a drug that successfully minimizes the possibility of contamination of the drug, the vial and the stopper between storage and administration in U.S. Pat. No. 4,614,515, which patent is assigned to the same assignee as the present invention. In this system the drug or medicament is sealed within a vial by a removable stopper in the vial opening. Positioned over the stopper in the vial opening is a removable diaphragm. Circumscribing the outside of the vial is a skirt member, which is in frictional contact with the wall portion of the vial. The diaphragm is connected to the skirt member so that access to the interior of the vial may be obtained by either separating the diaphragm from the skirt member and piercing the stopper with the point of a cannula, or separating the diaphragm from the skirt member and removing the stopper from the vial opening. The separation of the diaphragm from the skirt member is accomplished by the use of fragile sections circumscribing that portion of the skirt member, which connects the portion of the skirt member in frictional contact with the wall portion of the vial and the diaphragm. Once the diaphragm has been removed from its position over the stopper, the stopper may be removed from the vial and the contents of the vial added to an intravenous administration system without compromising sterility of the drug, the vial or the stopper.

A system disclosing an apparatus for making a direct addition of a medicament or drug to a flexible container for eventual use as either a primary or secondary fluid source in I.V. therapy is disclosed in U.S. Pat. No. 4,614,267, which patent is also assigned to the same assignee as the present invention.

There is a need for facilitating the connection of such a vial to a syringe assembly. There is also a need for facilitating the introduction of a diluent into the drug-containing vial of such a system. There is further a need to provide the above capability for activation at the point of use so as to minimize the time between mixing and delivery to the patient.

SUMMARY OF THE INVENTION

A storage and delivery system is provided that includes a vial assembly constructed and arranged to contain a substance such as a drug or medicament. The substance is sealed within a vial associated with the vial assembly by a pierceable stopper whereby the flowable substance may be extracted therefrom through a needle inserted into the vial through the stopper. Circumscribing the outside of the vial is a skirt member that is in frictional contact with a wall portion of the vial. The system includes a syringe assembly having a cannula extending longitudinally therethrough. An adapter assembly attaches the vial to the syringe assembly in a manner that permits communication between the interior of the vial and the cannula extending through the syringe. The substance may be extracted from the vial through the cannula or a diluent may be added to the vial through the cannula.

The adapter assembly means includes an adapter member attachable to the vial. The syringe assembly includes a lock member attachable to the adapter member. The adapter member releasably engages the lock member. A needle hub member associated with the adapter member supports a needle that pierces the stopper as the adapter member is attached to the vial. The needle hub member is provided with the female portion of a luer connector that is received by a complementary male portion of a luer connector, associated with the lock member and in fluid communication with the cannula such that the male portion is received by the female portion as the adapter member is attached to the lock member.

A system is further provided for separately storing and subsequently mixing the contents of at least two containers in one of the containers. The system includes a first container or vial assembly, of the type described above, containing a first substance, and a second container containing a flowable second substance. The second container has a pierceable stopper or plunger in sealing engagement with an open end thereof, whereby the contents of the second container may be extracted therefrom through a cannula inserted thereinto through the plunger means. A syringe assembly, of the type described above, extends between the first and second containers. The syringe assembly has a first end portion attachable to the second container so as to permit communication between the interior of the second container and a first end of a cannula extending through the syringe assembly as the first end of the cannula extends through the plug means. An adapter assembly connects the vial assembly to the syringe assembly in the same manner as described above.

DESCRIPTION OF THE DRAWINGS

A better understanding of the drug storage and delivery system of the invention will be had by reference to the drawings wherein.

DESCRIPTION OF THE PREFERRED EMBODIMENTS

FIGS. 1-4 illustrate a preferred embodiment of a drug storage and delivery system 10 constructed in accordance with the invention that includes a drug storage vial assembly 12, a syringe assembly 14 and an adapter assembly 16 interconnecting the vial assembly to the syringe assembly.

Figure 3:
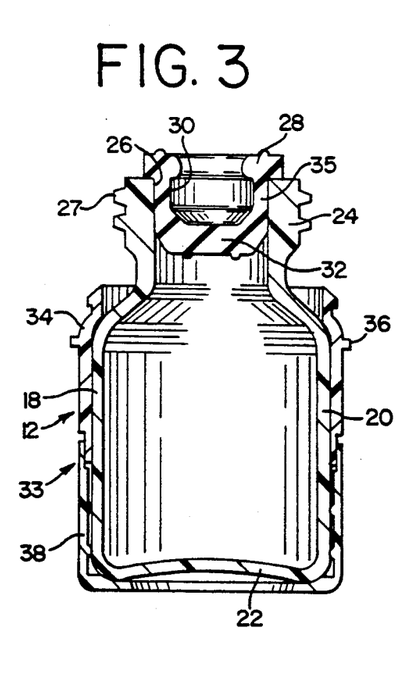
FIG. 3 is an elevational view in vertical section of a vial assembly of the type compatible for attachment to an adapter assembly of the present invention, with the removable portion of the cap being removed.

The present invention is particularly designed to cooperate with a vial assembly 12 of the type and construction disclosed in the above mentioned U.S. Pat. No. 4,614,515, the disclosure of which patent is specifically incorporated herein by reference. Referring specifically to FIG. 3, the vial assembly is shown with the protective top section and the tear strip removed and ready for use by a pharmacy or health care personnel. The vial assembly includes a drug-containing glass vial 18 having a wall portion 20, a bottom or end portion 22, and a tapered neck portion 24 defining an opening 26. While a generally cylindrically shaped vial is shown, it will be understood that the specific shape of the vial is not critical to the system of the present invention. The top or neck of the vial 18 is provided with threads 27 circumscribing the outside portion of opening 26.

A removable, pierceable stopper 28 seals opening 26 of vial 18 and maintains the sterility of the drug or medicament contained therein. Stopper 28 is shown as being substantially U-shaped in cross-section in the preferred embodiment; that is having a depressed portion 30 oriented so that the bottom section 32 thereof is facing toward the interior of the vial and a wall portion 35 that seals against the opening 26.

Vial 18 is encased in a protective cover assembly 33, only a portion of which is shown in FIG. 3. Assembly 33 includes a skirt member 34 having an inner surface in frictional engagement with vial 18. Circumscribing skirt member 34 is a ring of ratchet teeth 36, the purpose of which will hereinafter become more apparent. The bottom 22 of the vial 18 is protected by a shroud member 38 which is constructed to overlap a portion of skirt member 34 and to frictionally engage vial 18.

Figures 1, 2:
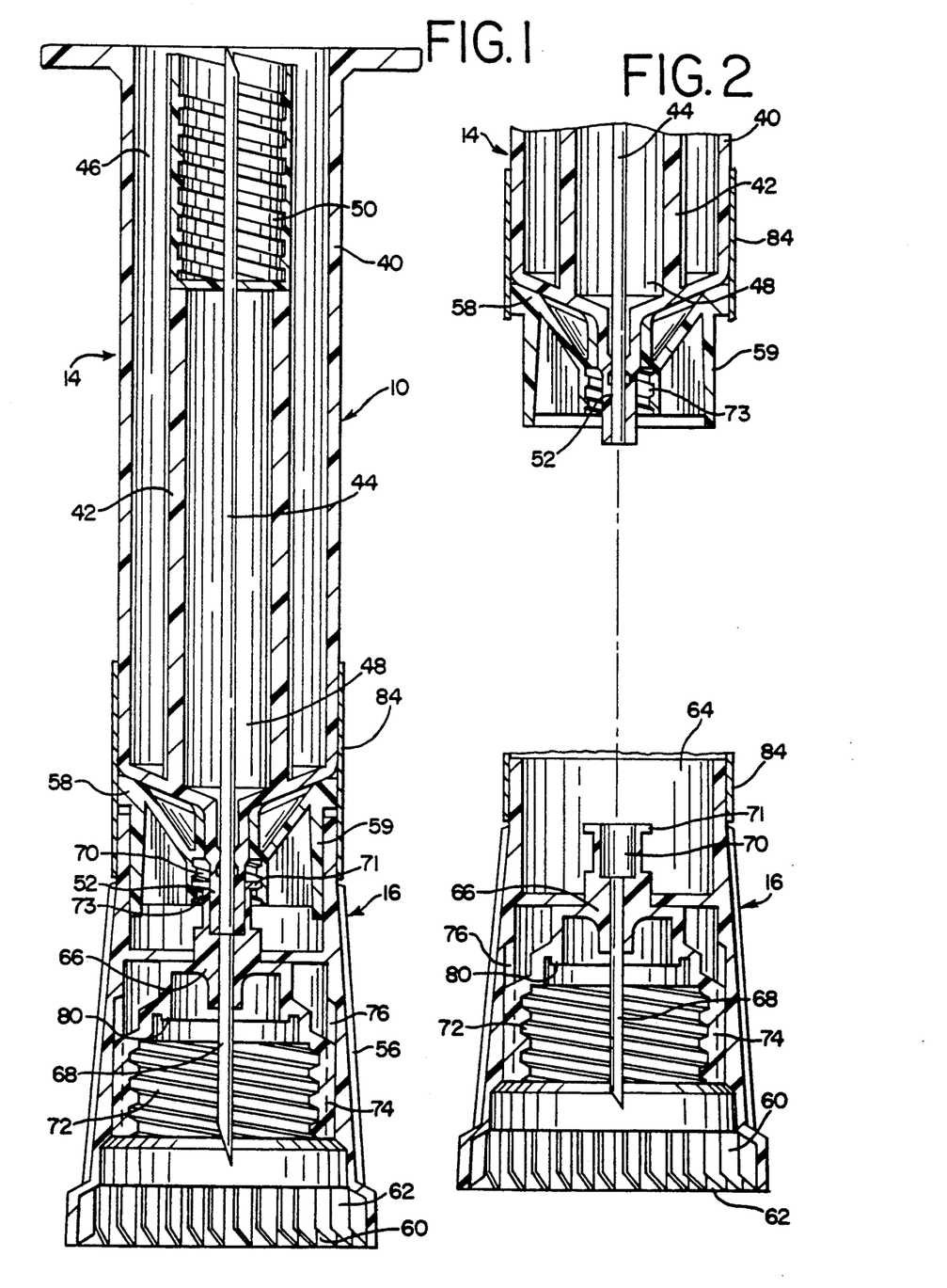
FIG. 1 is an elevational view in vertical section of the syringe assembly and the adapter assembly of the drug storage and delivery system constructed in accordance with the present invention.
FIG. 2 is an elevational view in vertical section of a portion of the syringe assembly and the adapter assembly shown in FIG. 1 in a separated condition.

Syringe assembly 14 is of known construction and is formed with a cylindrical outer housing or barrel 40 having a cylindrical member 42 integrally formed therein. A cannula 44 extends longitudinally through member 42. Syringe assembly 14 has a first or open rear end portion 46 and a second or closed front end portion 48. The end portion of member 42 adjacent end portion 46 of syringe assembly 14 is provided with internal threads 50. The end portion of cannula 44 adjacent end portion 48 of syringe assembly 14 is received by the male taper portion 52 of a luer fitting or connector formed at the end portion of member 42 adjacent end portion 48, as best seen in FIG. 2. The end portion 46 is provided with a removable cap member (not shown) to protect the sterility of the interior of the syringe assembly.

The adapter assembly 16 that interconnects the vial assembly 12 to the syringe assembly 14 comprises an adapter member 56. Adapter member 56 is attachable to threads 27 of vial 18. Lock member 58 is part of syringe assembly 14 and is attachable to adapter assembly 16.

As best seen in FIG. 2, adapter member 56 has an open end portion 60 that is suitably configured to receive and engage skirt member 34. End portion 60 is formed with a ring of internally formed ratchet teeth 62 that cooperate and engage ratchet teeth 36 associated with skirt member 34, so as to preclude disconnection of member 56 from member 34 after they have been connected in a manner to be hereinafter discussed. Adapter member 56 has an open end portion 64 that is suitably configured to receive and frictionally engage lock member 58. Open end 60 is provided with a suitable removable cap member (not shown) to maintain the sterility of the interior of adapter member 56.

A needle hub member 66 is rigidly secured within adapter member 56 in a suitable manner, such as by ultrasonic welding or the like. Needle hub member 66 is formed to receive and rigidly support a needle or cannula member 68 that extends toward opening 60 of adapter member 56. The forward end of needle 68 terminates a short distance from open end portion 60. The rear end of needle 68 is received in a female taper portion 70 of a luer fitting or connector that is configured to threadedly receive male portion 52 thereinto. An external thread member 71 is formed at the end of portion 70. Needle hub member 66 is provided with an internally threaded recess portion 72 in facing relationship to open end 60 that is configured to threadedly receive threads 27 circumscribing the outside portion of opening 26 of vial 18. A plurality of circumferentially spaced splines 74 are formed on member 66 that are received in elongated internal recesses 76 formed in adapter member 56 to preclude rotational movement of these members with respect to each other.

Lock member 58 is formed to be received about the luer fitting male taper portion 52 and is attached to the end portion 48 of syringe assembly 14 in a suitable manner, such as by ultrasonic welding or the like. Lock member 58 is formed with a cylindrical portion 59 that has an outer diameter that permits its receipt and frictional engagement within open end portion 64 of adapter member 56 as the luer fitting male portion 52 is received by the luer fitting female portion 70. The male and female luer fittings are locked as the thread member 71 is received in a cooperating internally threaded recess portion 73 formed integral with lock member 58.

The brief discussion of the operation of the embodiment of the invention shown in FIGS. 1-4 that follows sets forth the cooperation between the above disclosed structural elements. This embodiment facilitates utilization of the vial assembly 12 with a syringe assembly 14. The vial assembly 12 containing the desired drug is received from the pharmacy and the protective top section (not shown) and tear strip (not shown) are removed to ready the vial assembly for use, as shown in FIG. 3.

The syringe assembly 14 and adapter assembly 16 is preferably inventoried in the pharmacy in the connected condition as shown in FIG. 1, with suitable protective caps (not shown) covering the respective ends thereof. The syringe assembly 14 is attached to the adapter assembly 16 by securing the male taper luer fitting 52 to the female taper luer fitting 70. These fittings are locked in position as thread member 71 is threaded within threaded recess portion 73. In so doing, cylindrical portion 59 of lock member 58 is received within open end portion 64. A suitable label 84 may be applied around the connected unit to display product identification and instructions and to assist in maintaining the connection between the syringe assembly 14 and the adapter assembly 16. The needle 68 is in fluid communication with cannula 44.

Figure 4:
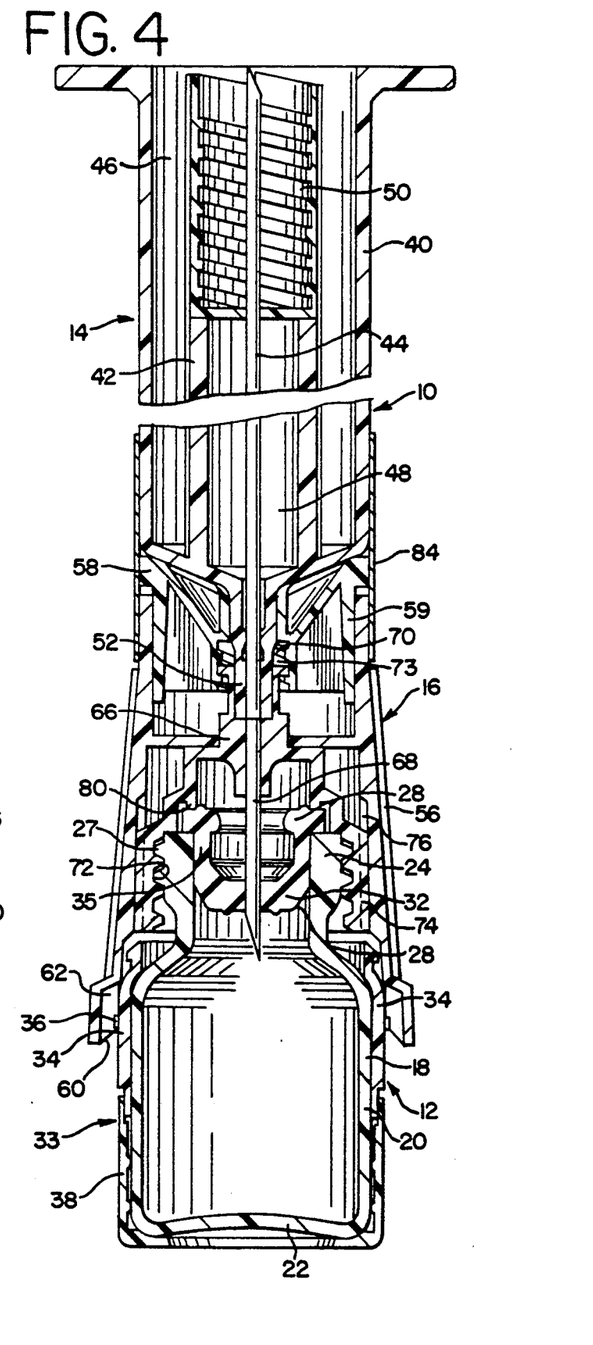
FIG. 4 is an elevational view in vertical section showing the vial assembly shown in FIG. 3 attached to the adapter assembly and syringe assembly of the present invention.

The connected syringe assembly and adapter assembly unit may be attached to the vial assembly either in the pharmacy or at the location of administration. Referring to FIG. 4, in connecting the syringe assembly/adapter assembly unit to the vial assembly, the neck portion 24 of vial 18 is positioned in recess 72 of member 66 such that threads 27 are engaged by the cooperating threads formed in recess 72. In so doing, needle 68 penetrates bottom section 32 of stopper 28 and communicates with the interior of vial 18 and ratchet teeth 36 engage ratchet teeth 62 in a manner that precludes the unscrewing of neck portion 24 from recess 72. The bottom of recess 72 is preferably formed with a detent portion 80 which contacts and retains stopper 28 securely in position within opening 26 of vial 18.

The drug or medicaments contained in vial 18 may be drawn and administered directly to a patient or otherwise directed to a suitable drug administration device.

Figures 5, 6:
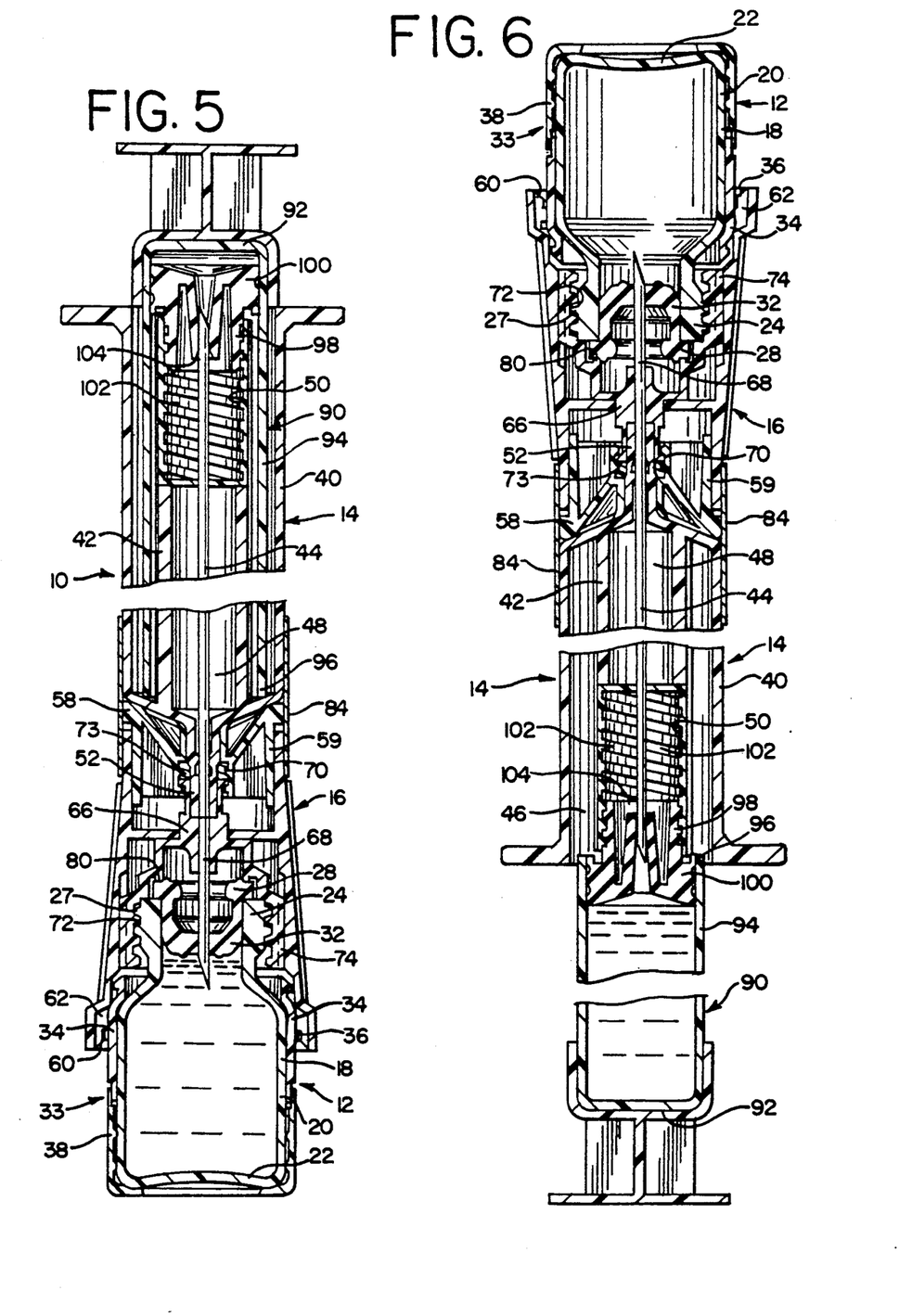
FIG. 5 is a view similar to FIG. 4 showing the drug storage and delivery system of the present invention attached to a diluent containing container shown in a position delivering diluent into the vial assembly.
FIG. 6 is a view of the system shown in FIG. 5 showing the system in a position delivering the mixed solution from the vial assembly back into the container.
Figures 7, 8:
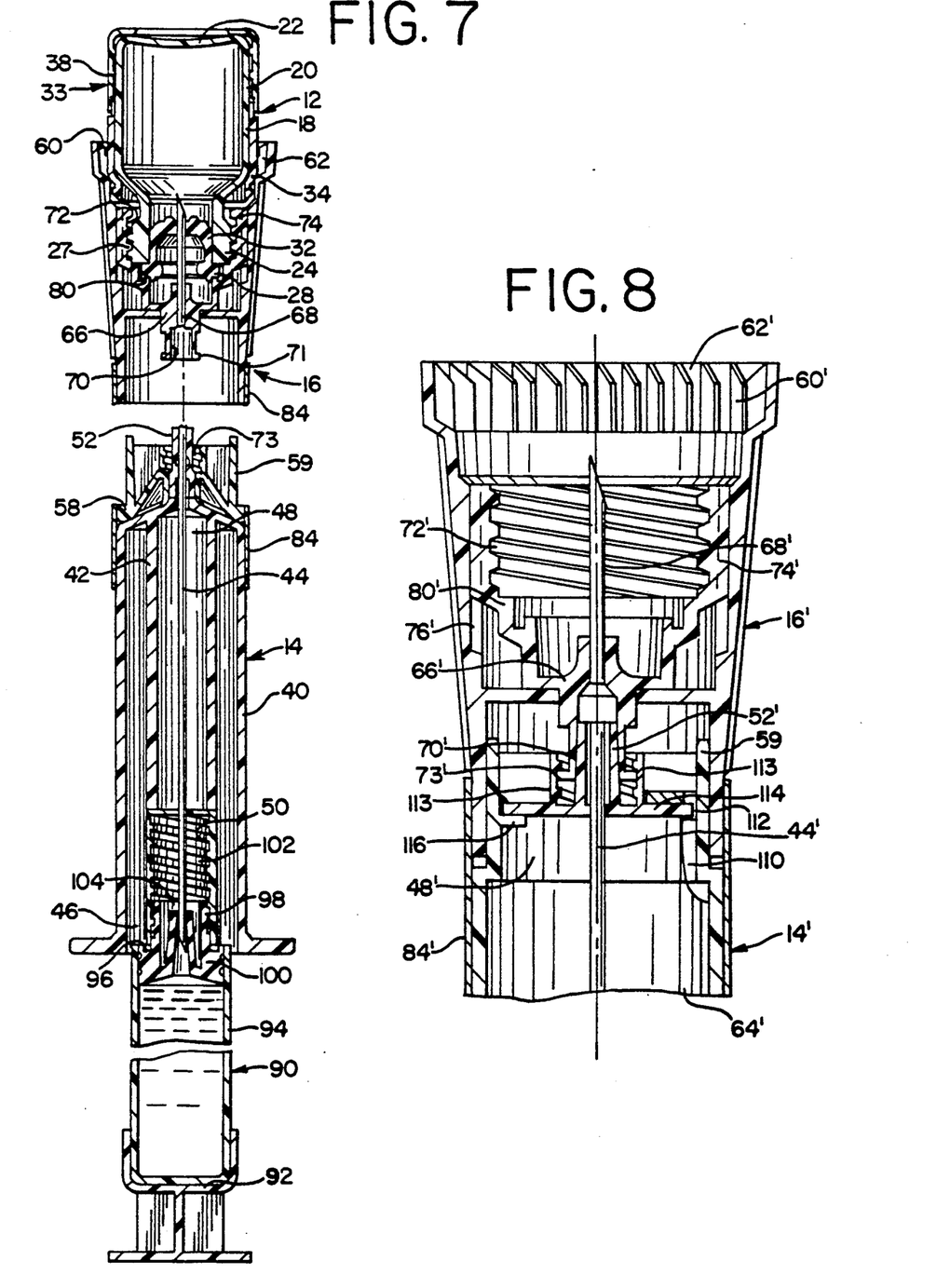
FIG. 7 is a view similar to FIG. 5 showing the vial assembly and the adapter member separated from the lock member and syringe assembly.
FIG. 8 is an elevational view in vertical section showing two alternative embodiments of the invention.

Referring to FIGS. 5-7, the above described system is shown attached to a diluent containing container 90 to permit delivery of a diluent into vial 18 and to permit receipt subsequent delivery of a mixed solution from the vial. Container 90 is formed with a closed end portion 92, a wall portion 94 and an open end portion 96. A pierceable stopper or plunger 98 is slidably received in container 90 in contact with wall portion 94 to seal the open end portion 96. Plunger 98 has a sealing section 100 that is dimensioned to sealingly engage the inner surface of wall portion 94 as it moves between the end portions of container 90. Plunger 98 also has a threaded connecting section 102, having external threads that are configured to be received by threads 50 formed at the end portion of member 42 adjacent end portion 46 of syringe assembly 14. Plunger 98 is formed with a diaphragm portion 104 through which cannula 44 may pass and communicate with the interior of container 90. Container 90 is filled with a suitable drug or diluent that is intended to be mixed with the drug contained in vial assembly 12.

The brief discussion of the operation of the embodiment of the invention as shown in FIGS. 5-7 that follows sets forth the cooperation between the disclosed structural elements. This embodiment permits utilization of the system, as shown in FIG. 1, in a manner that facilitates the mixing of a diluent or a drug with the drug contained in vial 18. The drug contained in vial 18 may be in the form of a powder that must be mixed with a diluent prior to its administration.

The syringe assembly 14 and adapter assembly 16 are attached to the vial assembly in the manner as previously discussed. This unit is attached to a container 90 that has been previously filled (usually in the factory) with the desired diluent or drug. Container 90 is attached to syringe assembly 14 by inserting and rotating threaded connection section 102 of the plunger 98 in the threaded end portion 50 of member 42. In so doing, the adjacent end cannula 44 pierces diaphragm portion 144 and extends into container 90.

The assembled system is preferably oriented with the vial assembly 12 on the bottom and the container 90 on top (as shown in FIG. 5), in order to facilitate the injection of the contents from container 90 into vial 18. All or some of the contents from container 90 is delivered through cannula 44 and needle 68 into vial 18 by moving container 90 into the chamber formed between housing 40 and cylindrical member 42 in syringe assembly 14. As the plunger member 98 moves towards the closed end portion 92, the contents of container 90 is directed into vial 18. The contents in vial 18 are mixed, and if the drug in vial 18 is in powdered form, it is dissolved by the diluent from container 90. This process may be facilitated by a repeated pumping of plunger 98 within container 90.

The mixed solution from vial 18 is directed back into container 90 by reversing the above procedure. The orientation of the assembled system is turned upside down with the vial assembly 12 on the top, as shown in FIG. 6. The container 90 is withdrawn from syringe member 14 causing plunger 98 to move towards the open end 96. In so doing, the mixed contents from vial 18 are directed through needle 68 and cannula 44 into container 90.

The vial assembly 12 and adapter assembly 16 are then disconnected from the syringe assembly 14 and container 90, as shown in FIG. 7. This is accomplished by withdrawing male luer fitting 52 from female luer fitting 70. In so doing, the label 84 is severed along a line adjacent the end of adapter member 56. The vial assembly and adapter assembly 16 are discarded and the syringe assembly and container 90 can then be operated as any other syringe system to administer the mixed contents from container 90 to a patient.

Referring to FIG. 8, two alternative embodiments of the invention are shown, one of them being to the right and the other being to the left of the vertical centerline. These embodiments differ from the above discussed embodiments only in the manner in which the lock member or portion associated with the end of the syringe assembly is constructed. The elements of these alternative embodiments that are common to the above discussed embodiments are identified with the same reference numeral followed by a prime (') sign.

In the embodiment to the right of the center line, the end portion 48' of syringe assembly 14' is formed with a ramp portion 110 and a detent portion 112. A cannula supporting member 113, having a male luer fitting portion 52' and a recess lock portion 73' formed integrally therewith, includes an end plate or portion 114. As member 113 is positioned in syringe assembly 14', the plate portion 114 snaps in place and is received in detent portion 112 as it rides long ramp portion 110.

In the embodiment to the left of the centerline, the end portion 48' of syringe assembly 14' is formed with an inwardly extending flange portion 116. A member 113 constructed as discussed above is positioned in syringe assembly 14' so that plate portion 114 contacts flange portion 116. Plate portion 114 is preferably secured to flange portion 116 and portion 59' by an ultrasonic weld.

Figure 9:
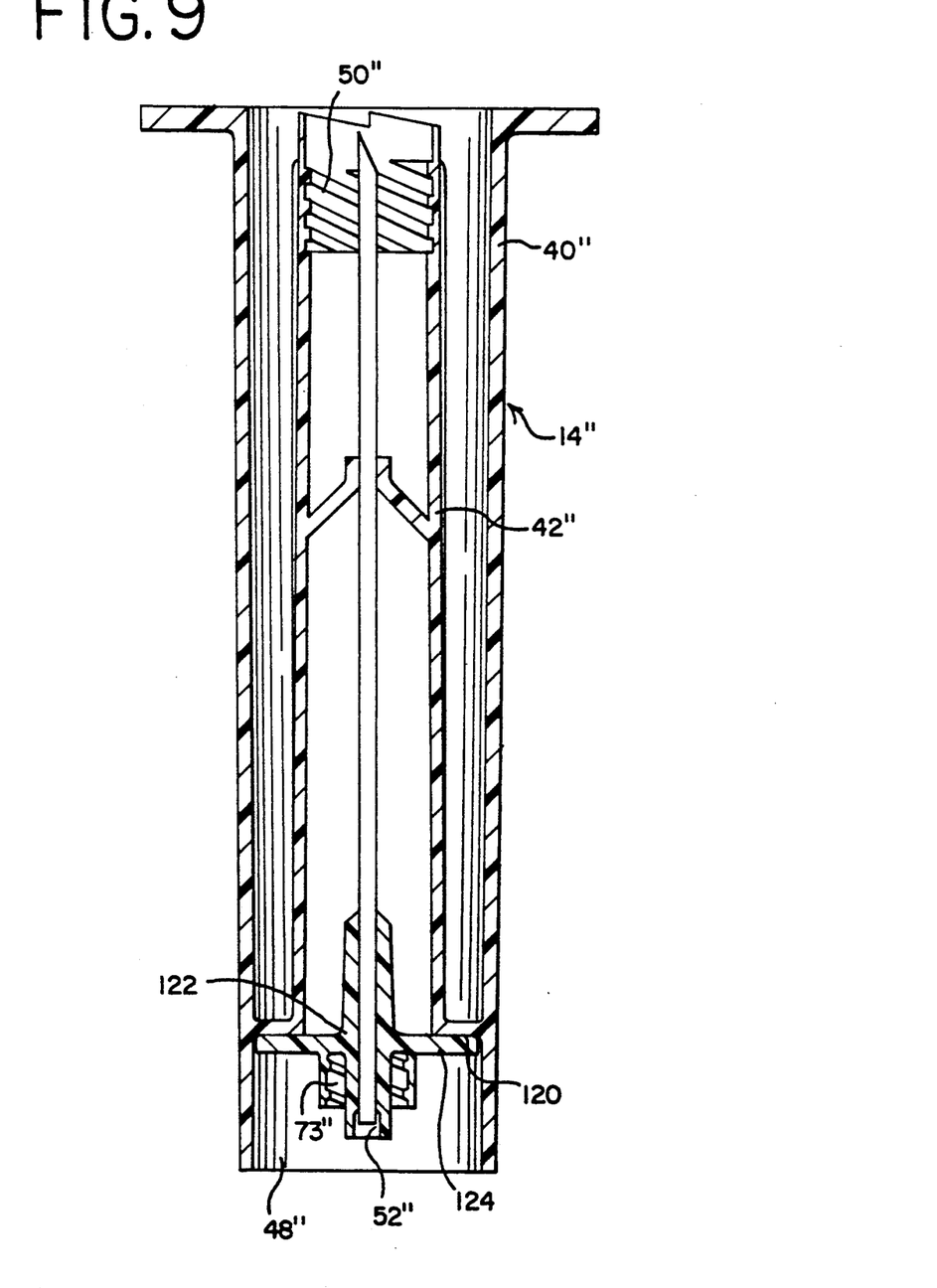
FIG. 9 is an elevational view in vertical section showing a further alternative embodiment of the invention.

Referring to FIG. 9, a further alternative of the invention is shown. This embodiment also differs from the above discussed embodiments only in the manner in which the lock member or portion associated with the end of the syringe assembly is constructed. The elements of this embodiment that are common to the above embodiments are identified with the same reference numeral followed by a double prime (") sign. The end portion 48" of syringe assembly 14" is formed such that the end portion of member 42" defines an annular surface 120. The inner diameter of end portion 48" is such that it may receive the end portion 64 of adapter member 56, which may have a reduced diameter to permit such a relationship. A cannula supporting member 122, having a male luer fitting portion 52" and a recess lock portion 73" formed integrally therewith, includes an end plate portion 124. As member 122 is positioned in syringe assembly 14", the plate portion 124 contacts surface 120. Plate portion 124 is preferably secured to surface 120 and the housing of syringe assembly 14" by an ultrasonic weld.

It will thus be seen that through the present invention there is now afforded a drug storage and delivery system in which the procedures between storage and administration of a drug are minimized. Activation of the drug delivery system by health care or pharmacy personnel is facilitated without the use of sophisticated or excessive procedures or prolonged exposure that might jeopardize sterility.

The foregoing invention can now be practiced by those skilled in the art. Such skilled persons will appreciate that the drug storage and delivery system of the present invention is not necessarily restricted to the particular embodiments presented herein. The scope of the present invention is to be defined by the terms of the following claims in the spirit and meaning of the preceding description.

What is claimed is:
1. A storage and delivery system for a flowable substance, comprising:
   (a) a vial having a threaded opening, a wall portion and an end portion constructed and arranged to contain a flowable substance;
   (b) a pierceable stopper in sealing engagement with said opening in said vial whereby the flowable substance may be extracted from said vial through a needle inserted into said vial through said stopper;
   (c) a syringe assembly having a generally cylindrical housing and a cannula supported in said housing and extending longitudinally therethrough along an axis thereof;
   (d) an adapter assembly including an adapter member for attaching said vial to said syringe assembly so as to permit communication between the interior of said vial and said cannula extending through said syringe;
   (e) a skirt member frictionally engaging said wall portion of said vial, said skirt member having ratchet means associated therewith that cooperates with complementary ratchet means associated with said adapter member upon attachment of said adapter assembly to said vial so as to thereafter prevent disengagement of said vial from said adapter assembly;
   (f) a lock member for attaching said adapter member to said syringe assembly wherein said adapter member releasably engages said lock member;
   (g) a needle hub member associated with said adapter member and supporting said needle that pierces said stopper as said adapter member is attached to said vial, said vial opening being threaded with said needle hub member threadedly receiving said threaded opening as said adapter member is attached to said vial; and
   (h) a fitting portion that cooperates with said lock member to provide fluid communication between said needle and said cannula as said adapter member is attached to said lock member.

2. The invention as defined in claim 1 wherein said needle hub member includes a detent portion for retaining said stopper in place within said opening as said adapter member is attached to said vial.

3. The invention as defined in claim 1 wherein said needle hub member is rigidly secured to said adapter member by ultrasonic welding.

4. The invention as defined in claim 1 wherein said adapter member has elongated recess portions that cooperate with complementary splines associated with said needle hub member to prevent rotation of said needle hub member with respect to said adapter member.

5. The invention as defined in claim 1 wherein said fitting portion of said needle hub member is a female portion of a luer connector in fluid communication with said needle and said lock member includes a complementary male portion of a luer connector in fluid communication with said cannula, such that said male portion is received by said female portion as said adapter member engages said lock member.

6. The invention as defined in claim 5 wherein said lock member is formed with an annular portion that is received within said adapter member as said adapter member engages said lock member.

7. The invention as defined in claim 1 wherein said lock member is formed integrally with said syringe assembly.

8. A system for separately storing and subsequently mixing the contents of at least two containers in one of the containers, said system comprising:
   (a) a first container having an opening, a wall portion and an end portion constructed and arranged to contain a first substance, said first container having a pierceable stopper in sealing engagement with said opening whereby the contents of said first container may be extracted therefrom through a needle inserted thereinto through said stopper;
   (b) a second container having an opening, a wall portion and an end portion constructed and arranged to contain a flowable second substance, said second container having a pierceable plug in sealing engagement with said opening whereby the contents of said second container may be extracted therefrom through a cannula inserted thereinto through said plug;
   (c) a syringe assemby having a generally cylindrical housing and a cannula supported in said housing and extending longitudinally therethrough along an axis thereof, said syringe assembly having a first end portion attachable to said second container so as to permit communication between the interior of said second container and a first end of said cannula as said end extends through said plug; and
   (d) an adapter assembly means including an adapter member with complementary ratchet means for attaching said first container to said syringe assembly so as to permit communication between a second end of said cannula and the interior of said first container through a needle inserted through said stopper; and
   (e) a skirt member frictionally engaging said wall portion of said first container, said skirt member having ratchet means associated therewith that cooperates with complementary ratchet means associated with said adapter member upon attachment of said adapter assembly to said first container so as to thereafter prevent disengagement of said first container from said adapter assembly.

9. The invention as defined in claim 8 wherein said adapter assembly means includes an adapter member attachable to said vial and a lock member for attaching to said adapter member to said syringe assembly.

10. The invention as defined in claim 9 wherein said adapter member releasably engages said lock member.

11. The invention as defined in claim 10 wherein said adapter member has a needle hub member associated therewith, said needle hub member supporting said needle that pierces said stopper as said adapter member is attached to said vial, and a fitting portion that cooperates with said lock member to provide fluid communication between said needle and the second end of said cannula as said adapter member is attached to said lock member.

12. The invention as defined in claim 11 wherein said opening of said first container is threaded and said needle hub member threadedly receives said threaded opening as said adapter member is attached to said vial.

13. The invention as defined in claim 12 wherein said needle hub member includes a detent portion for retaining said stopper in place within said opening as said adapter member is attached to said vial.

14. The invention as defined in claim 9 wherein said first container has a skirt member in frictional engagement with said wall portion, said skirt member having ratchet means associated therewith that cooperates with complementary ratchet means associated with said adapter member upon attachment of said adapter assembly to said first container so as to thereafter prevent disengagement of said first container from said adapter assembly.

15. The invention as defined in claim 11 wherein said needle hub member is rigidly secured to said adapter member by ultrasonic welding.

16. The invention as defined in claim 11 wherein said adapter member has elongated recess portions that cooperate with complementary splines associated with said needle hub member to prevent rotation of said needle hub member with respect to said adapter member.

17. The invention as defined in claim 11 wherein said fitting portion of said needle hub member is a female portion of a luer connector in fluid communication with said needle and said lock member includes a complementary male portion of a luer connector in fluid communication with said second end of said cannula, such that said male portion is received by said female portion as said adapter member engages said lock member.

18. The invention as defined in claim 17 wherein said lock member is formed with an annular portion that is received within said adapter member as said adapter member engages said lock member.

19. The invention as defined in claim 8 wherein said plug has a threaded portion that is received by a cooperating threaded portion formed in said first end portion of said syringe member.

20. The invention as defined in claim 19 wherein said first end of said cannula pierces said plug as said plug is threadedly received by said syringe member.

21. The invention as defined in claim 10 wherein said second container is cylindrical and said plug is slidably received within said second container such that as said plug moves towards the end portion of said second container the second substance container therein is directed through said cannula and said needle into said first container.

22. The invention as defined in claim 21 wherein said second container is received in said syringe assembly as said plug moves towards said end of said second container.

23. The invention as defined in claim 9 wherein said lock member is formed integrally with said syringe assembly.

* * * * *